US006258555B1

(12) United States Patent
Burnham et al.

(10) Patent No.: US 6,258,555 B1
(45) Date of Patent: Jul. 10, 2001

(54) DNA ENCODING ACV SYNTHETASE

(75) Inventors: Martin Karl Russell Burnham, Collegeville, PA (US); Alison Jane Earl, Steyning; John Henry Bull, Cheshire, both of (GB); David John Smith, Turku (FI); Geoffrey Turner, Sheffield (GB)

(73) Assignee: Beecham Group p.l.c. (GB)

( * ) Notice: Subject to any disclaimer, the term of this patent is extended or adjusted under 35 U.S.C. 154(b) by 0 days.

(21) Appl. No.: 08/909,108

(22) Filed: Aug. 11, 1997

Related U.S. Application Data

(62) Continuation of application No. 08/286,931, filed on Aug. 8, 1994, now abandoned, which is a continuation of application No. 07/799,764, filed on Nov. 27, 1991, now abandoned, which is a continuation of application No. 07/725,911, filed on Jul. 3, 1991, now abandoned, which is a continuation-in-part of application No. 07/382,640, filed as application No. PCT/GB88/01083 on Aug. 21, 1989, now abandoned.

(30) Foreign Application Priority Data

Dec. 9, 1987 (GB) .................................................... 8728811

(51) Int. Cl.[7] .......................... C12P 37/00; C12N 15/80; C12N 1/15; C12N 15/52
(52) U.S. Cl. ............................. 435/43; 435/47; 435/69.1; 435/252.3; 435/254.1; 435/254.11; 435/254.3; 435/254.5; 435/320.1; 435/471; 435/476; 435/484; 536/23.2; 536/23.7; 536/23.74
(58) Field of Search .................................. 536/23.1, 23.2, 536/23.7, 23.74; 435/43, 47, 69.1, 252.3, 254.1, 254.11, 254.3, 254.5, 320.1, 471, 476, 484

(56) References Cited

U.S. PATENT DOCUMENTS

| 5,108,918 | 4/1992 | Groenen et al. ............................ 435/6 |
| 5,462,862 | 10/1995 | Groenen et al. ..................... 435/69.1 |

FOREIGN PATENT DOCUMENTS

| 0200425 | 12/1986 | (EP) . |
| 0225128 | 6/1987 | (EP) . |
| 0233715 | 8/1987 | (EP) . |
| 0281391 | 9/1988 | (EP) . |
| 0288325 | 10/1988 | (EP) . |

OTHER PUBLICATIONS

D. Ramon et al., *Gene*, vol. 57, (1987) pp. 171–181.
Samson et al., *Nature*, vol. 318, (Nov. 14, 1985) pp. 191–194.
Malpartida et al., *Nature*, vol. 325, (Feb. 26, 1987) pp. 818–821.
Banko et al., *Am. Chem. Soc.*, vol. 109 (1987)pp2858–2860.
Samson et al., *Biotechnology*, vol. 5 No. 11 (Nov. 1987) pp 1207–1208, 1211, 1213, 1214.
Carr et al., *Gene*, vol. 48 Nos. 2–3 (1986) pp. 257–266.
Kurzatkowski et al., *Chemical Abstract*, vol. 96 (1982) pp. 414 ab 15894w.
Makins et al., *J. Gen. Microbiol.*, vol. 122, pp. 339–343 (1981).
Makins et al., *J. Gen. Microbiol.*, vol. 129, pp. 3027–3033 (1983).
Normansell et al., *J. Gen. Microbiol.*, vol. 112, pp. 113–126 (1979).
Martin et al., *Microbiol. Rev.*, vol. 44 pp. 230–251 (1980).
Brownlie et al., *J. Gen. Microbiol.*, vol. 132, pp. 3221–3229 (1986).
Caddick et al., *EMBO Journal*, vol. 5(5), pp. 1087–1090 (1986).
Smith et al., *Biotechnology*, vol. 8, pp. 39–41 (1990).
Smith et al., *EMBO Journal*, vol. 9, No. 3, pp. 741–747 (1990).
Smith et al., *EMBO Journal*, vol. 9, No. 9, pp. 2743–2750 (1990).

*Primary Examiner*—David Guzo
(74) *Attorney, Agent, or Firm*—Zoltan Kerekes; Stephen Venetianer; Charles M. Kinzig

(57) ABSTRACT

DNA encoding the gene for the synthetase enzyme capable of generating δ (L-a-aminoadipyl)-L-crysteinyl-D-valine (ACV) from its constituent amino acids was obtained from several penicillin and cephalosporin producing organisms, e.g. *Penicillium chrysogenum*, cephalosporium and a Flavobacterium species. The DNA was used to prepare recombinant vectors comprising the ACV synthetase gene and hosts transformed with such vectors. The ACV synthetase gene can form part of a gene cluster comprising other genes involved in -β-lactam biosynthesis and the production of penicillin by expression of the entire biosynthetic gene cluster for the synthesis of penicillin from primary amino acids is described. Suitable hosts in which expression can take place include heterologous hosts which are naturally non-producers of penicillin.

17 Claims, 7 Drawing Sheets

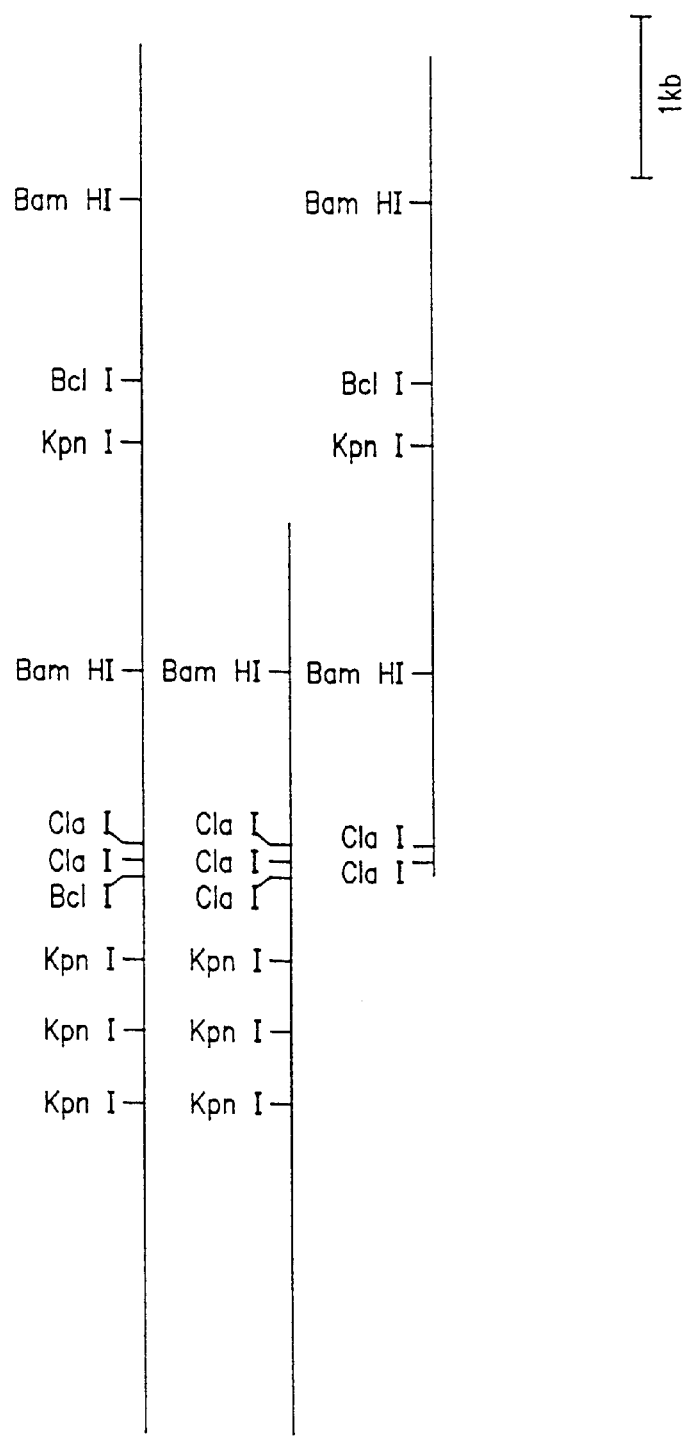

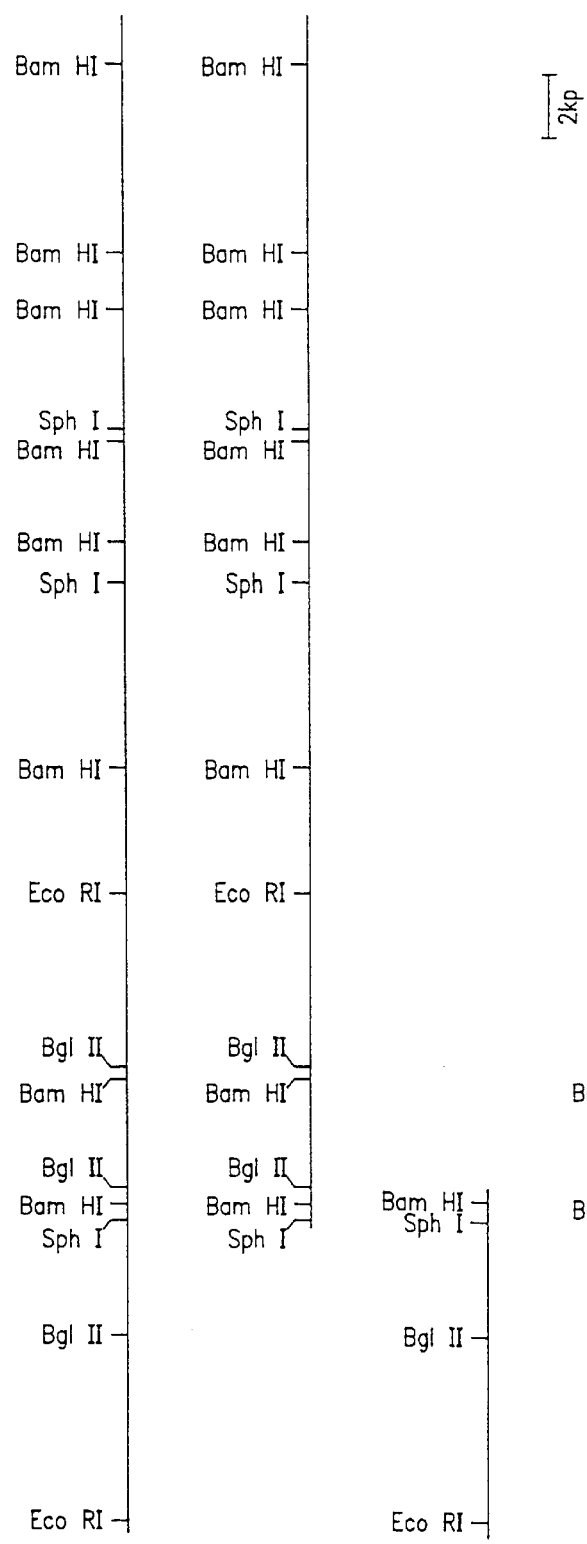

DNA ENCODING ACV SYNTHETASE

This application is a continuation of application Ser. No. 08/286,931, filed Aug. 8, 1994, now abandoned, which is a continuation of Ser. No. 07/799,764, filed Nov. 27, 1991, now abandoned, which is a continuation of Ser. No. 07/725,911, filed Jul. 3, 1991, now abandoned, which is a continuation-in-part of application Ser. No. 07/382,640, filed Aug. 21, 1989, now abandoned, which is a 371 application of PCT/GB88/01083, filed Dec. 9, 1988.

The present invention relates to DNA molecules, and to recombinant vectors for use in the transformation of a microbial host. In particular, the invention relates to biosynthetic genes for enzymes involved in penicillin biosynthesis, vectors comprising such genes, host cells transformed with the vectors, and the use of such host cells in penicillin production.

It has been established that the biosynthetic pathways of penicillins and cephalosporins (including cephamycins) are closely related. Isopenicillin N is an intermediate in the biosynthesis of both groups of compounds and is formed by the action of a 'cyclase' enzyme on the tripeptide δ (L-α-aminoadipyl)-L-cysteinyl-D-valine (sometimes referred to as LLD-ACV or, more simply, ACV as used hereinbelow). The intermediate isopenicillin N may be converted either to penicillin G or, by the action of an 'epimerase' enzyme, to penicillin N and it is from the latter that various cephalosporins and cephamycins may be derived by a multi-step pathway following an initial ring-expansion with an 'expandase' enzyme. A recent summary of the state of the art is given by J. F. Martin and P. Liras in *Trends in Biotechnology*, 1985, 3, 39–44.

The generation of the intermediate tripeptide ACV from its constituent amino acids is the least well understood and most difficult step to study of the entire pathway as reported by Adlington et al (*Biochem. J.*, 1983, 213, 573–576) and reviewed by S. E. Jensen in CRC *Critical Reviews in Biotechnology*, 1986, Vol. 3, Part 3, pages 277–310, and Nuesch et al (*Ann. Rev. Microbiol*, 1987, 41, 54).

As is now well known, by means of recombinant DNA techniques, it is possible to insert into a host cell DNA carried on a vector with the result that the transformed host may become endowed with the capacity to synthesise whatever protein(s) or enzyme(s) the gene(s) carried on the insert DNA may encode. (For a full discussion of recombinant DNA methodology, and a glossary of the terms used therein, see 'Principles of Gene Manipulation' by R. W. Old and S. B. Primrose, 3rd Edition, Blackwell Scientific Publications, 1985).

The isolation and expression in *E. coli* of the isopenicillin N synthetase (cyclase) gene from *C. acremonium* has been reported by S. M. Samson et al (Nature, 1985, 318, 191–194).

In addition, the isopenicillin N synthetase (IPNS) gene of *Penicillin chrysogenum* has been isolated and sequenced by Carr et al. (*Gene*, 1986, 48, 257–266).

The isolation and expression of certain genes of *S. clavuligerus* ATCC 27064 which are involved in the biosynthesis of β-lactams has been disclosed in European Patent Application Publication No. 0 233 715.

Hitherto, however, no DNA has been specifically identified as being of use in the production of an enzyme involved in the synthesis of ACV.

The present invention provides DNA comprising a gene encoding ACV synthetase.

As used herein the term 'gene encoding ACV synthetase' or 'ACV synthetase gene' is used to describe DNA which codes for an enzyme involved in the biosynthesis of ACV from its precursors.

The DNA of the invention may be isolated as described hereinbelow, from total or chromosomal DNA of organisms well known in the art which produce penicillins and/or cephalasporins, for example Pencillium, Aspergillus, Flavobacterium, Cephalosporium, and Streptomyces species. It will, of course, be understood that the DNA of the invention has been separated from the majority of such chromosomal DNA and is not in its 'natural' state, i.e. the form in which it occurs in nature. In one aspect, the DNA of the invention is in isolated and substantially purified form and/or consists essentially of the ACV synthetase gene.

In addition to the ACV synthetase gene, the DNA of the invention may additionally comprise further genes involved in the biosynthesis of penicillin and cephalosporin β-lactams, in particular the isopenicillin N synthetase (IPNS) gene and/or the acyltransferase (ACT) gene. The DNA of the invention may also comprise regulatory elements or regulatory genes involved in the biosynthesis of penicillin and cephalosporin β-lactams or may contain flanking DNA which has no particular or known function.

In a particular aspect, the DNA of the invention comprises the entire biosynthetic gene cluster for the production of a penicillin when the gene cluster is expressed in a suitable host organism, especially a fungal host. It will be appreciated that the said gene cluster has been separated from the majority of flanking chromosomal DNA and is not in its natural state.

As used herein the term "penicillin" includes isopenicillin N and also encompasses penicillins such as penicillins V and G, which may be formed when the host organism is cultured in the presence of a suitable side-chain precursor, for example phenoxyacetic acid or phenylacetic acid.

The present invention further provides a recombinant vector capable of transforming a host cell, which vector comprises the DNA of the invention. Preferably the said vector is a high expression vector capable of expressing high levels of gene transcript.

In another aspect of the invention there is provided a host cell, especially a fungal host, transformed with the recombinant vector of the invention.

The invention further provides a process for transforming a host cell with a recombinant vector according to the invention which comprises mixing together the host and recombinant vector under conventional transformation conditions.

BRIEF DESCRIPTION OF FIGURES

In order to define the invention clearly, reference is made to the following figures in which:

FIG. 3 is a restriction map of a portion of *S. clavaligerus* ATCC 27064 DNA, restriction fragments thereof being shown in FIGS. 4 (DNA cloned in a recombinant plasmid designated pBROC 138) and 5 (DNA cloned in a recombinant plasmid designated pBROC 137);

FIG. 8 is a restriction map of DNA comprising genes involved in penicillin and cephalosporin biosynthesis in *S. clavuligerus* ATCC 27064;

FIG. 9 is a restriction map of a fragment of that DNA cloned in a recombinant plasmid designated pBROC 371;

FIG. 10 is a restriction map of a fragment of that DNA cloned in a recombinant plasmid designated pBROC 401;

FIG. 11 shows the region of *S. clavuligerus* DNA to which fragment TPS/VE of Flavobacterium sp. SC 12,154 hybridises;

In the Figures, the abbreviations Bam HI, Sph I etc. are conventional abbreviations for restriction endonucleases (see Old and Primrose, loc.cit.), and the approximate length in kilobases (Kb) of the DNA, as determined by sizing experiments carried out by agarose gel electrophoresis, is indicated. It should be understood that FIGS. 1 to 14 are not necessarily intended to show all the possible restriction sites present on the DNA illustrated. In FIGS. 12–13 dotted lines indicate restriction fragments which, when probed as described hereinbelow, hybridised less strongly than fragments indicated by unbroken lines.

In a preferred aspect, the DNA of the invention is obtained from a Penicillium, Aspergillus, Cephalosporium, Flavobacterium or Streptomyces species, more preferably from Penicillium, Aspergillus or Flavobacterium. Advantageously the DNA of the invention is obtained from *P. chrysogenum*.

Figures 12, 13:
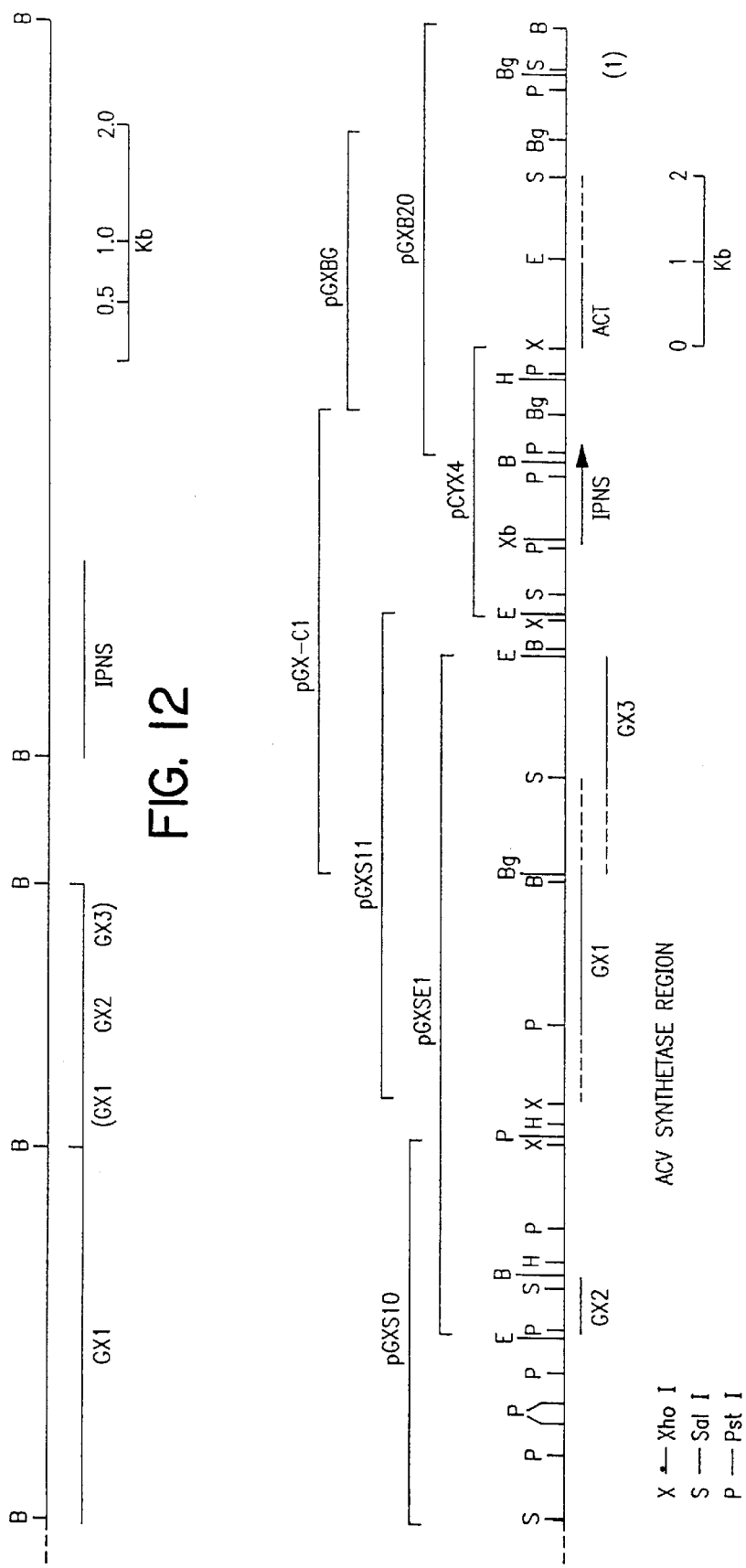
FIGS. 12 and 13 show a cross hybridisation map of the region of Flavobacterium DNA of FIG. 1 which contains the ACV and cyclase genes [FIG. 12] and the corresponding region of *P.chrysogenum* DNA [FIG. 13] in a cosmid clone designated pCX3.2: the cross-hybridising regions (marked GX1, GX2 and GX3) and the extent of plasmid sub-clones of *P.chrysogenum* DNA designated pGXS10, pGXE1, pGXS11, pGX-C1, pCYX4, pGXBG and pGXB20 are indicated.

In a specific embodiment of the invention there is provided *P. chrysogenum* DNA (I) or a restriction fragment derived therefrom comprising an intact ACV synthetase gene, the said DNA (I) having the configuration of restriction sites hereinunder shown in FIG. 13.

The DNA (I) may be obtained by methods described hereinbelow, from *P. chrysogenum*.

A particular subfragment of the DNA(I) is the Eco RI-Eco RI fragment spanning the regions marked GX1, GX2 and GX3.

In a further specific embodiment of the invention there is provided Flavobacterium sp. SC 12,154 DNA or a restriction fragment derived therefrom comprising an intact ACV synthetase gene, the said DNA having the configuration of restriction sites hereinunder shown in FIG. 1.

In a particular aspect, the Flavobacterium DNA has the structure (II) as shown in FIG. 12.

A particular subfragment of (II) is the Bam HI—Bam HI fragment spanning the regions marked GX1, GX2 and GX3.

In yet a further specific embodiment of the invention there is provided *S.clavuligerus* DNA (III) or a restriction fragment derived therefrom comprising the ACV synthetase gene, the said DNA (III) having the configuration of restriction sites hereinunder shown in in FIG. 11.

Figure 14:
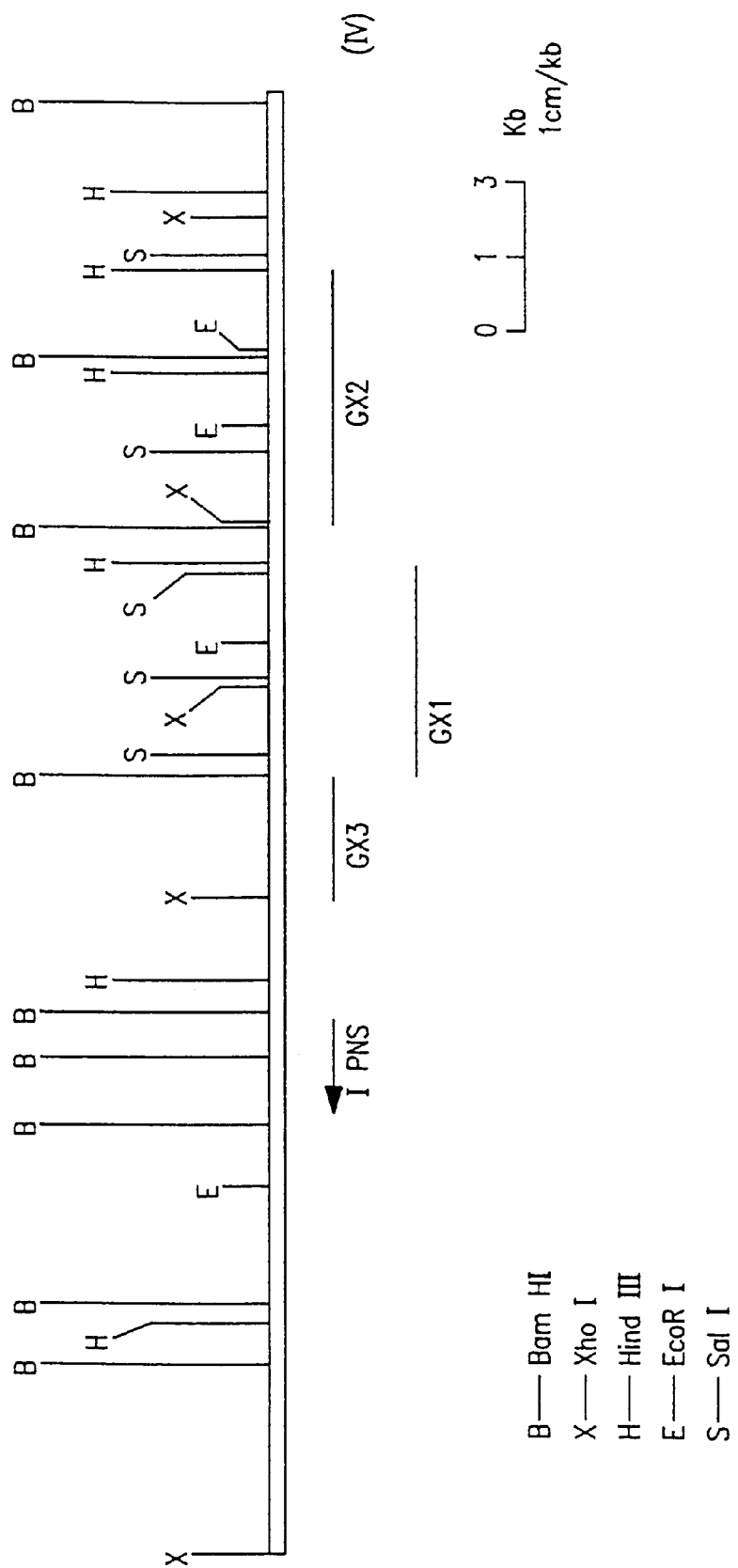
FIG. 14 shows a cross hybridisation map of *A. nidulans* DNA, indicating the regions (marked GX1, GX2, and GX3) which cross-hybridise with the corresponding regions of *P. chrysogenum* DNA shown in FIG. 13.

In a still further specific embodiment of the invention there is provided *A.nidulans* DNA (IV) or a restriction fragment derived therefrom comprising an intact ACV synthetase gene, the said DNA (IV) having the configuration of restriction sites hereunder shown in FIG. 14.

Restriction fragments of the DNA (I), (II), (III), or (IV) according to the invention may be derived from the DNA segments (I) to (IV) by cleavage with appropriate restriction enzymes by known methods.

In a particular aspect, the invention provides a recombinant vector capable of transforming a host cell, which vector contains insert DNA (I), (II), (III) or (IV) or a restriction fragment derived therefrom containing an intact ACV synthetase gene.

The DNA of the invention, for example as characterized in FIG. 11, FIG. 1, FIG. 12, FIG. 13 or FIG. 14, or a suitable restriction fragment derived therefrom, may be ligated to any suitable vector. For the production of ACV synthetase the vector should be capable of transforming or transfecting a host cell in which the ACV gene may be expressed.

Normally the said vector is a plasmid, for example a plasmid derived from a streptomycete, or is a temperate or virulent phage.

An example of a suitable vector is pIJ 702 (molecular weight 8.9 megadaltons), a high copy plasmid described by Katz, E. et al in *J. Gen. Microbiol.*, 1983, 129, 2703–2714, and available from the John Innes Institute, Norwich, England.

An example of a suitable temperate phage is that known as ØC31, described by Lomovskaya, N. D., Chater, K. F., Mkrtumian, N. M., in *Bacteriol. Rev.*, 1980, 44, 206–229.

It is advantageous to use a filamentous fungal vector for expression of the ACV synthetase gene in an ascomycete or deuteromycete host. Suitable vectors include p3SR2 carrying the amdS gene (Beri and Turner, *Current Genetics*, 1987, 11, 639–641; and pCAP2 which carried a pvr-4 marker.

The recombinant vectors of the invention may be prepared by standard techniques, for example by ligating the insert DNA characterized in FIG. 1, FIG. 11, FIG. 12, FIG. 13 or FIG. 14 or a suitable restriction fragment derived therefrom, to the chosen vector by any convenient method, for example by direct combination of cohesive ends, homopolymer tailing, or by means of a linker or adapter molecule.

It will be appreciated that recombinant vectors prepared according to the above methods may contain the insert DNA in one of two possible orientations. Recombinant vectors having the insert DNA in each orientation are included within the scope of the invention.

The invention further provides a process for obtaining DNA according to the invention from a penicillin or cephalosporin-producing micro-organism. The process comprises the steps of:

a) constructing a gene library from chromosomal DNA fragments obtained from a penicillin or cephalosporin-producing micro-organism;

b) carrying out one or more hybridisation experiments in order to select from the said library clones which contain the DNA of the invention; and c) isolating the DNA of the invention.

In the above process the micro-organism may suitably be any micro-organism which produces penicillins and/or cephalosporins via the intermediate tripeptide ACV. Such organisms include, for example *P. chrysogenum*, Cephalosporium, *A. nidulans, C. acremonium*, Streptomyces species, for example *S. clavuligerus*, and Flavobacterium species, for example Flavobacterium sp. SC 12,154.

The gene library may be prepared by conventional 'shotgun' methodology by:

(a) partial digestion of the chromosomal DNA of a penicillin or cephalosporin producing micro-organism with one or more suitable restriction endonucleases, for example Sau 3AI;

(b) size fractionation to give fragments of appropriate length;

(c) ligation of the fragments into a vector to obtain a recombinant vector; and (d) transformation or transfection of a suitable host with the recombinant vector.

As described herein, transformation or transfection may be carried out by conventional methods well known in the art.

Size fractionation may suitably be carried out on a sucrose gradient and fragments within chosen size limits may be selected.

In a preferred aspect a 'cosmid library' may be prepared by selecting fragments of about 30 to 50 kb, for example about 35–40 kb, in length and ligating the said fragments into a cosmid vector, for example the vector pCAP2 (available from G. Turner, University of Bristol).

In order to identify clones in the gene library which contain the ACV synthetase gene, it is necessary to use a labelled probe capable of hybridising to that gene.

Normally the probe is radio-labelled, for example with, $^{32}$P. Radio-labelling may be carried out by standard techniques, for example 5'- or 3'-end labelling or nick translation.

One method of obtaining the DNA of the invention is to carry out cross-hybridisation experiments between a biosynthetic gene cluster isolated from a gene library of DNA fragments from a first micro-organism which produces cephalosporins and total DNA from a second micro-organism which produces penicillins but not cephalosporins. Since the biosynthetic pathway in the two organisms diverges after the formation of isopenicillin N the only biosynthetic genes expected to hybridise will be those coding for ACV synthetase and isopenicillin N synthetase. The two genes may be distinguished by further experiments, most conveniently by hybridisation with a probe which is specific for the isopenicillin N synthetase gene, such as the IPNS gene of *P. chrysogenum* or a fragment thereof (Carr et al., *Gene*, 1986, 48, 257–266). Thereafter the ACV gene from the first micro-organism may be isolated by standard techniques and DNA comprising that gene or fragment thereof may be used as a probe to isolate the ACV gene from a gene library of the second or any other suitable β-lactam producing micro-organism. Experiments to express the proteins from the ACV DNA of either the first or second organism with subsequent enzymic assay or complementation of a mutant should be carried out to establish the identity of the DNA, as described hereinbelow.

In a preferred aspect the first micro-organism is Flavobacterium sp SC 12,154 and the second micro-organism is *P. chrysogenum*.

So that the skilled person does not have to repeat the cross-hybridisation experiments hereinabove described DNA according to the invention has been deposited in a culture collection under the terms of the Budapest Treaty. The DNA is designated pCX3.2 which carries an approximately 38 Kb insert of *P. chrysogenum* CMI 314652 DNA in the cosmid pCAP2. The insert comprises the whole gene cluster shown in FIG. 13, i.e. carries not only the ACV synthetase gene but also the isopenicillin N (IPNS) gene and the acyl transferase (ACT) gene of *P. chrysogenum*. pCX3.2 was introduced into *E.coli* DH1 and the transformed host was deposited on Nov. 23rd, 1987, at the National Collection of Industrial Bacteria under the Accession number NCIB 12591. Strain NCIB 12591 and pCX3.2 form further aspects of the present invention.

pCX3.2 may readily be obtained from the above deposited micro-organism and, if desired, subfragments may be prepared which do not carry the IPNS and ACT genes.

It will be apparent that sub-fragments of the ACV synthetase gene will also be of value as gene probes. Such subfragments are included within the scope of the present invention.

If required, evidence that the DNA of the invention has been isolated may be obtained by using it to repair certain penicillin or cephalosporin-producing 'blocked mutants' which lack the capability to synthesise ACV. Useful mutants for this purpose include *A.nidulans* strains, especially that designated NPA5 containing the mutation npeA 0022 (Makins et al., *J.Gen. Microbiol.*, 1981, 122, 339).

To obtain Flavobacterium DNA according to the invention it is first necessary to have access to Flavobacterium so. SC 12,154. The micro-organism, kindly given to us by Squibb from their culture collection, is a Gram-negative rod, the properties of which were first described by P. D. Singh et al., *Journal of Antibiotics*, 1982, Vol XXXV No. 10, pages 1397–1399. Suitable fermentation conditions for the micro-organism were also reported in that paper.

A reisolate of Flavobacterium sp. SC 12,154 has been deposited in the National Collections of Industrial and Marine Bacteria, Aberdeen, Scotland, the deposit (NCIB 12339; deposition date Oct. 15th, 1986) being made under the terms of the Budapest Treaty on the International Recognition of the Deposit of Micro-organisms for the Purposes of Patent Procedure.

A 'gene library' of Flavobacterium sp. SC 12,154 chromosomal DNA fragments may be prepared by the method described hereinabove.

Advantageously a 'cosmid library' of Flavobacterium sp. SC 12,154 may be prepared by selecting fragments of about 30 to 50 kb and ligating the said fragments into a cosmid vector, for example pMMB 33, following the method of Frey et al (*Gene*, 1983, 24, 299–308).

Alternatively a library of smaller pieces of Flavobacterium sp. SC 12,154 chromosomal DNA, typically 3–15 kb in length, preferably 4–7 kb in length, may be prepared by ligating the said fragments into a plasmid vector, for example paT153.

Before clones which contain Flavobacterium DNA according to the invention are selected, it is advantageous to clone a number of genes involved in the biosynthesis of penicillins and cephalosporins by probing the gene library with a piece of DNA which encodes enzymes involved in the biosynthesis of β-lactams produced by micro-organisms other than Flavobacterium sp. SC 12,154. Suitable probes include genes encoding cyclase, epimerase or expandase enzymes, or fragments of such genes including synthetic oligonucleotides. Suitable micro-organisms from which the probe may be obtained include Streptomyces species, in particular *S. clavuligerus* ATCC 27064. The IPNS gene of *P. chrysogenum* or a sub-fragment thereof may also advantageously be used as a probe.

Additional DNA may be present in the probe provided the additional DNA does not cause 'background' hybridisation. For example the probe may form part of a recombinant vector. Any convenient vector may be used provided the vector DNA does not have appreciable homology with the vector used to form the library from which positive clones are to be selected.

Suitably the probe DNA has the configuration of restriction sites shown in FIG. 3 or preferably is a fragment thereof comprising the whole or part of a gene encoding the expandase or epimerase enzymes of *S. clavuligerus* ATCC 27064.

Such preferred fragments include DNA having the configuration of restriction sites shown in FIGS. 4 and 5 and suitable sub-fragments thereof.

Figure 6:
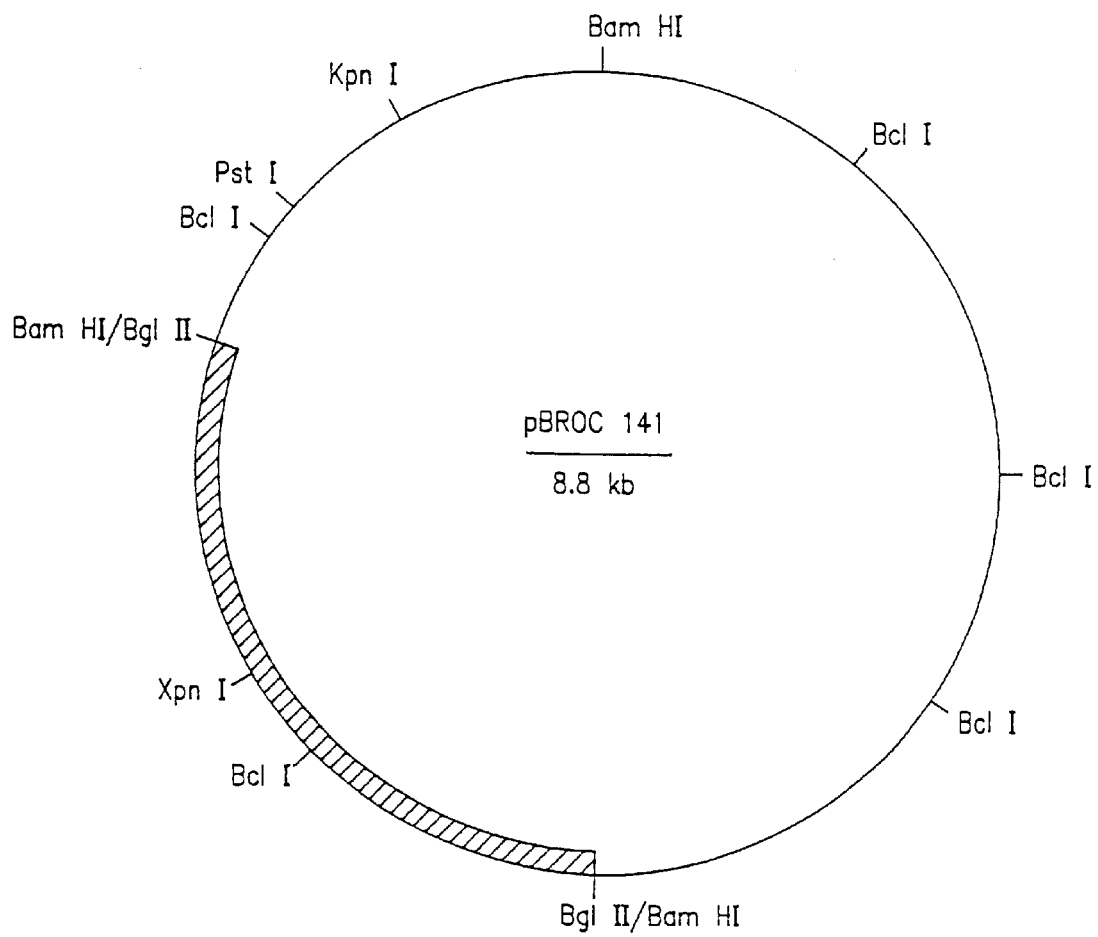
FIG. 6 is a restriction map of a recombinant plasmid designated pBROC 141.
Figure 7:
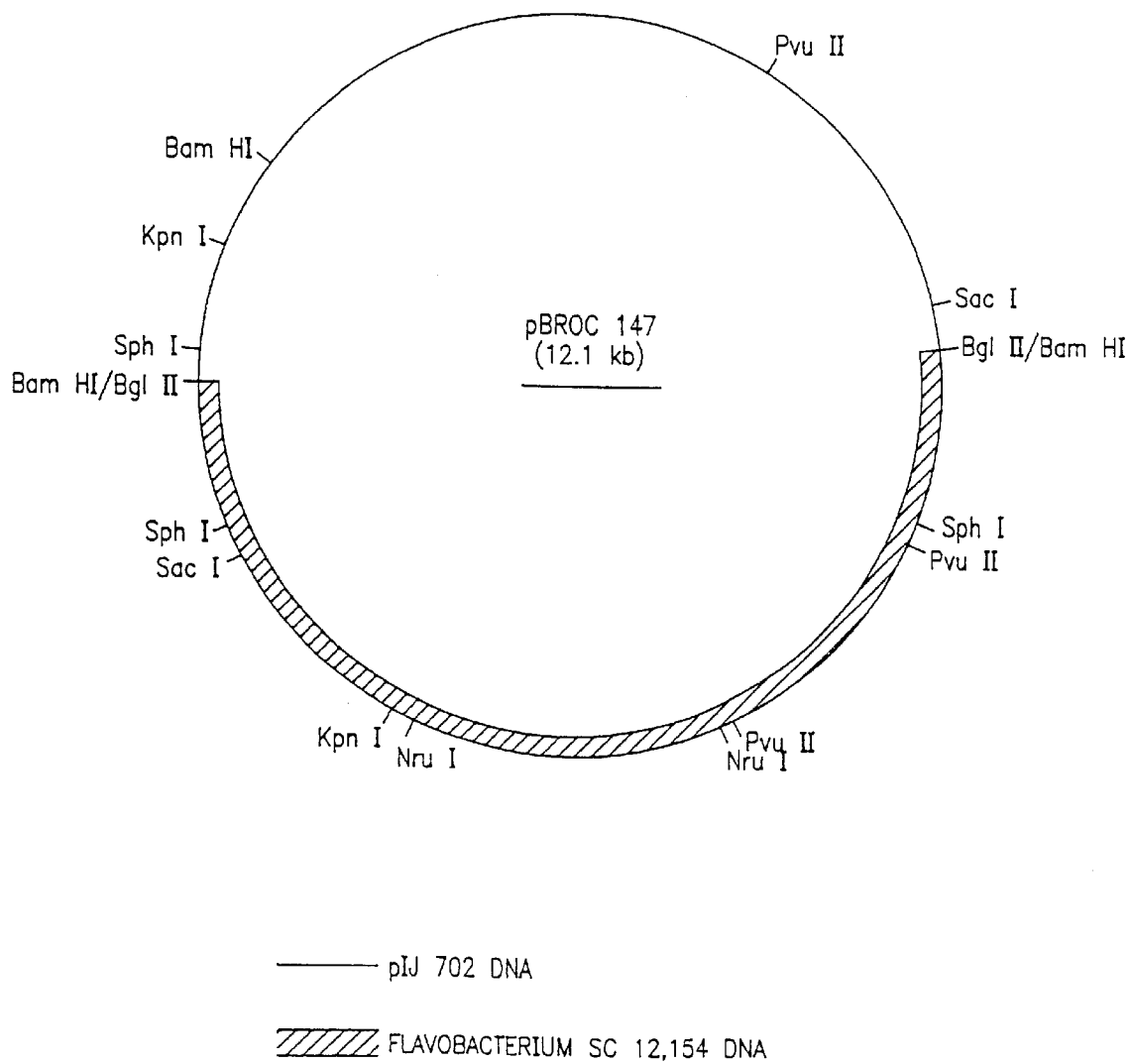
FIG. 7 is a restriction map of a recombinant plasmid designated pBROC 147.

A particular sub-fragment which may be used as a probe is the 3 kb Bam HI fragment of the DNA shown in FIG. 5. When cloned into pIJ 702 that fragment yields a recombinant plasmid designated pBROC 141 (see FIG. 6).

Another sub-fragment which is useful as a probe is a Kpn I-Pst I (2.1 kb) DNA fragment obtained from pBROC 141.

The *S. clavuligerus* chromosomal DNA shown in FIGS. 3–5 may be obtained as described in European Patent Application Publication No. 0 233 715.

To select those clones from the Flavobacterium gene library which contain DNA according to the invention, the labelled probe may be used in a conventional hybridisation experiment and positive colonies may be identified, for example by autoradiography. Recombinant vectors may be isolated from each positive colony by conventional methods. On digestion of the recombinant vectors with suitable restriction enzymes, the Flavobacterium sp. SC 12,154 DNA contained in each vector may be identified, sized, and 'mapped' by cleavage with a variety of restriction enzymes in the conventional manner in order to check that it contains the DNA of the invention. Two or more 'overlapping' inserts so isolated (i.e. inserts having common DNA) which are wholly or partly embraced within the DNA of the invention but which individually are too small to contain an intact gene may be fused together by cleavage at a common restriction site followed by ligation (e.g. with DNA ligase) in conventional manner.

It will, of course, be understood that the probe may conveniently be a piece of Flavobacterium sp. SC 12,154 chromosomal DNA, which may be used to identify Flavobacterium sp. SC 12,154 chromosomal DNA of the invention extending beyond the region in the probe. That technique will be known to those skilled in the art and is sometimes referred to as 'chromosome walking'. Thus, in one preferred aspect, a relatively short fragment of Flavobacterium sp. SC 12,154 DNA may be isolated by probing a library of Flavobacterium sp. SC 12,154 chromosomal DNA fragments contained in a plasmid vector, for example pAT153, with a suitable piece of *S. clavuligerus* chromosomal DNA, for example that shown in FIG. 5 or a sub-fragment thereof. The Flavobacterium sp. SC 12,154 DNA fragment so isolated, for example the DNA cloned in pBROC 143 (FIG. 2), may then be used as a probe to isolate from a cosmid library a longer piece of DNA containing the DNA of the invention or a suitable fragment thereof.

Demonstration that the DNA isolated contains the ACV gene may be obtained by direct cross hybridisation studies with DNA from other organisms coding for equivalent enzymes, for example *P. chrysogenum* and *S. clavuligerus* as hereinabove described.

The DNA for such hybridisation studies is suitably total chromosomal DNA obtained from *P. chrysogenum* NRRL 1951.

This may be used to identify two regions [marked GX1–GX3; and IPNS in FIG. 12] on the Flavobacterium DNA which hybridise indicating that the DNA carries genes involved in the early stages of penicillin and cephalosporin biosynthesis. The identity of one of these regions as the Flavobacterium isopenicillin N synthetase (IPNS) gene may be established by probing with the IPNS gene from *P. chrysogenum* or a fragment thereof; the remaining region which cross-hybridises thus corresponds to gene(s) involved in ACV biosynthesis.

The region of Flavobacterium DNA corresponding to the ACV biosynthetic gene or a fragment thereof (for example that designated GX1) may be used as a probe to isolate from a *P. chrysogenum* gene library clones which contain the ACV gene [see FIG. 13].

The production of the ACV synthetase enzyme may be achieved by inserting the DNA of the invention into a suitable vector and transforming any suitable host, for example *E. coli*, *S. lividans* 66 (DSM 1567), or *P.chrysogenum*, with the thus formed recombinant DNA.

As mentioned hereinabove, a filamentous fungal vector will normally be used for expression of the ACV synthetase gene in *P.chrysogenum*.

The ACV synthetase enzyme, when prepared by recombinant DNA techniques as hereinabove described, forms another aspect of the present invention. Preferably it is obtained in highly purified form.

The enzyme may be isolated and purified by conventional methods.

The DNA of the invention and vectors containing same may find use in many areas of industrial activity. That also applies to host micro-organisms transformed with said vectors. The ACV synthetase enzyme also has industrial application. Recombinant vectors containing said DNA may be of value, when transformed into suitable hosts, in the production of genetically modified micro-organisms which synthesize increased amounts of valuable antibiotics such as penicillins G and V, or in the generation of novel or hybrid antibiotics via the process of gene transfer (see for example D. A. Hopwood et al., Nature, 1985, 314, 642–644).

The invention thus has the important advantage that it is possible to introduce into a suitable host the ACV synthetase gene and, optionally linked thereto, other or all other biosynthetic genes involved in penicillin biosynthesis. In that way it is possible to increase the copy number or the level of expression of the ACV gene in hosts which already possess that gene or to repair a mutation which may be present causing the host to be blocked in the step of ACV synthesis.

According to one aspect of the invention, therefore, there is provided a method of producing a penicillin from a host cell which is naturally a producer of penicillin or from a non-producing mutant of such a host blocked at the step of ACV synthesis, which method comprises the steps of:

(a) transforming the said host or said non-producing mutant thereof with a vector comprising the DNA of the invention; and (b) cultivating the transformants so formed under appropriate conditions so that production of the penicillin takes place.

Preferably the host in the above method is a fungal host, especially *P. chrysogenum*.

In addition, when the DNA of the invention comprises the entire biosynthetic gene cluster for the production of a penicillin as hereinabove described, it is also possible to use the clustered genes to obtain penicillin from a suitable fungal host which is naturally a non-producer of penicillin.

Thus, in another aspect, the invention provides a method for producing a penicillin in a fungal host which is naturally a non-producer of penicillin, which method comprises the steps of:

(a) isolating DNA carrying the entire biosynthetic gene cluster for the production of the penicillin;

(b) inserting the DNA into a suitable vector to form a recombinant vector;

(c) transforming the said host with the recombinant vector; and (d) cultivating the transformed host under appropriate conditions so that the penicillin is produced.

As used herein, the term "fungal host" includes ascomycetes (including hemiascomycetes such as the saccharomycetaceae or yeast family), basidiomycetes, zygomycetes and deuteromycetes.

Particularly suitable fungal hosts are filamentous ascomycetes and deuteromycetes, for example Penicillium, especially *P. chrysogenum*, Cephalosporium, especially *C. acremonium*, Aspergillus and Neurospora species.

Preferred fungal hosts which are naturally non-producers of penicillin include *Aspergillus niger* and *Neurospora crassa*.

It will be appreciated that suitable fungal hosts have access to all the amino acids required for the biosynthesis of ACV.

Preferably the recombinant vector used in either of the above methods is pCX3.2.

Preferred penicillins which may be produced by the above methods include penicillins G and V.

From the foregoing description it will be appreciated that the present invention makes it possible to assemble a gene cluster (comprising ACV synthetase, IPNS, epimerase and expandase) which can be used in a method for the production of a cephalosporin when the genes in the cluster are expressed in a suitable host. Such a gene cluster forms a further aspect of the present invention, as do recombinant vectors carrying the gene cluster and hosts into which the gene cluster is transformed. Preferred hosts include Flavobacterium and Streptomyces species.

The IPNS, expandase and epimerase genes of Flavobacterium, for example of Flavobacterium sp. SC 12, 154, form yet another aspect of the present invention, as do recombinant vectors carrying the genes (individually or clustered) and hosts into which the recombinant vectors may be transformed.

In a further aspect, the DNA of the invention or a fragment thereof (not necessarily carrying an intact gene) may be combined, either by recombinant DNA techniques or by natural recombination processes, with a fragment of a gene involved in β-lactam biosynthesis to produce a hybrid gene capable of directing the synthesis of a hybrid enzyme. Such enzymes may be used in the production of novel antibiotics by processes analogous to those hereinbefore described.

The DNA of the invention may also be modified by the known techniques of site-directed mutagenesis (in a manner analogous to that described, for example, by G. Winter et al., *Nature*, 1982, 299, 756–758; or by Zoller and Smith, *Nucleic Acids Research*, 1982, 10, 6487–6500) to give DNA in which specific mutations and/or deletions have been effected. The mutated DNA may be used to obtain an increased yield (or titre) of known β-lactam antibiotics from a suitable host micro-organism that already produces such compounds. The mutated DNA may also be used to obtain novel or hybrid antibiotics by gene transfer, or used in the production of mutant enzymes (muteins) which may be used in the production of novel antibiotics by analogous processes to those hereinabove described.

It will be appreciated that such mutated DNA is within the scope of the invention.

The invention will now be illustrated by the following Examples.

PREPARATION 1

Cloning DNA Homologous to the S, cavuligerus Expandase Gene From Flavobacterium sp SC 12, 154

(a) Subcloning the S clavuligerus expandase gene from pBROC 137 onto pIJ 702

3 µg of pBROC 137 DNA [see European Patent Application Publication No. 0 233 715 and FIG. 5] was digested with Bam HI, Pst I and Pvu II restriction enzymes and the resulting fragments ligated with 0.5 µg Bql II digested pIJ 702 for 16 hours at 15° C. Aliquots of the ligation mix representing 100 nanograms of DNA were then transformed into S. lividans 66

Transformants were screened for their ability to express expandase enzymatic activity (as described in Preparation 7 of European Patent Application Publication No. 0 233 715). It was found that the 3 kilobase Bam HI DNA fragment of FIG. 5 closed into pIJ 702 was able to confer expandase activity upon S, lividans 66, especially when cloned in the orientation shown in pBROC 141 (see FIG. 6).

(b) Hybridization experiments $^{32}$p-labelled Kpn I/Pst I (2.1 kilobase) DNA fragment of pBROC 141 was used in Southern hybridization experiments with Bam HI digested total cellular DNA from the cephalosporin-producing Flavobacterium sp. SC 12,154 [see Singh, P. D. et. al (1982). J.Antibiotics 35(10) 1397–1399]. When non-hybridized $^{32}$p-labelled DNA was removed by washing with 2×SSC. 0.1% SDS at 70° C. it was found that the S.clavuligerus DNA hybridized to an approximately sized 6 kilobase fragment of Flavobacterium sp. SC 12,154 total cellular DNA.

In order to clone this fragment of Flavobacterium DNA, 100 micrograms of total cellular DNA was digested to completion with Bam HI, size-fractionated on sucrose gradients to give 5 to 7 kilobase fragments and subsequently cloned into the Bam HI site of pAT 153 [Twigg, A. J. and Sherratt, D. (1980) *Nature*, 283 216] in *E.coli*DH1. 400 *E.coli* DH1colonies carrying pAT 153 clones of Flavobacterium sp. 12,154 DNA obtained in this manner were screened for colony hybridization to the phosphorus $^{32}$p-labelled fragment of pBROC 141 DNA using the hybridization stringency described above.

Figure 2:
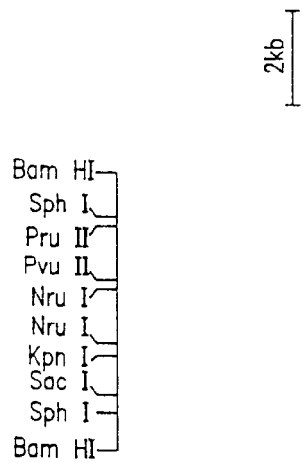
FIG. 2 is a restriction map of the CXI region of the DNA of FIG. 1.

Two hybridizing colonies were obtained which carried a 6.3 kilobase fragment of Flavobacterium DNA shown in FIG. 2 cloned into pAT 153. This plasmid was designated pBROC 143.

PREPARATION 2

The Expression of Enzymatic Activity by the Flavobacterium DNA of pBROC 143 in S.lividans 66

10 micrograms of pBROC 143 derived from *E.coli* DH1was digested with Bam HI restriction enzyme and ligated with 2 µg Bql II digested pIJ 702 DNA with subsequent transformation into S.lividans 66. In this manner, pBROC 147 and pBROC 148 (see Fig. 4), i.e. pIJ 702 carrying the Flavobacterium sp. SC 12,154 DNA in both possible orientations, were constructed.

S.lividans 66: pBROC 147, S.lividans 66: pBROC 148 and S.lividans 66: pIJ 702 were used to furnish cell free, particulate free, soluble enzyme preparations using the method described in Preparation 7 of European Patent Application Publication No. 0 233 715.

(a) Demonstration of Expandase Enzymic Activity by Bioassay.

Enzyme preparation from S.lividans 66: pIJ 702, S.lividans 66: pBROC 147 and S.lividans 66: pBROC 148 were used in ring expansion assay systems [as described in Jensen, S. E. et.al (1983) *Antimicrob.Aq.Chemother.* (24)3 307–312] to determine the presence of deacetoxy cephalosporin C synthetase.

Utilising the *E.coli* ESS/Penicillinase (DIFCO Penicillinase concentrate $10^4$ µ/ml) bioassay system described by these authors it could be shown that S.lividans 66: pIJ 702 and S.lividans 66: pBROC 148 extracts were unable to transform Penicillin N to penicillinase resistant antibiotics whereas the extract from S.lividans 66: pBROC 147 was able to carry out a substantial transformation in this respect.
(b) Demonstration of Expandase Enzymic Activity by High Pressure Liquid Chromatography (HPLC) Analysis Enzyme preparations from S.lividans 66: pIJ 702, S.lividans 66: pBROC 147 and S.lividans 66: pBROC 148 were used in ring expansion assay systems (See Jensen S. E. et. al, loc, cit.) in final volumes of 1.2 ml.

After 2 hours of incubation, 30 µl of glacial acetic acid was added with shaking and a de-proteinated supernatant was obtained by centrifugation (10,000 G for 5 minutes). This liquid was absorbed into a QAE-Sephadex column (1 ml volume). The resin was washed with 200 µl of water and 200 µl of 0.2M NaCl. The cephalosporin were eluted from the resin with a further 250 µl of 0.2M NaCl. Samples (20 µl) of these purified reaction products were analysed by HPLC using a $C_{18}$ reverse-phase Microbondapak column (Mobile phase 0.1M $NaH_2PO_4$, pH 3.2). Elution was carried out at 2 ml/min with U. V. detection at 260 n.m. Samples were analysed before and after treatment with cephalosporinase.

In this manner it was possible to show that whilst extracts from S.lividans 66 pIJ 702 and S.lividans 66: pBROC 148 were unable to convert penicillin N to deacetoxycephalosporin C, an extract from S.lividans 66: pBROC 147 transformed penicillin N to give a peak on HPLC with an identical retention time to authentic deacetoxycephalosporin C (9.6 minutes).

Demonstration of iso-Penicillin N epimerase Activity by Bioassay and HPLC

Using the iso-Penicillin N epimerase assay developed by Jensen, S. E. et.al [*Can. J Microbiol.* (1983) 29 (11) 1526–1531] it was possible to demonstrate that cell free, particulate free enzyme extracts from S.lividans 66: pBROC 147 and more especially from S.lividans 66: pBROC 148 were able to convert iso-Penicillin N to a chemical form at least ten times more active against *E.coli* ESS than iso-Penicillin N itself. A similar extract from S.lividans 66: pIJ 702 was unable to do this.

Bioassay of the reaction products on *E.coli* ESS/DIFCO Penicillinase [as in preparation 2(*a* )] showed that the extract from S.lividans 66: pBROC 147 was able to convert iso-Penicillin N to a penicillinase resistant antibiotic [shown by purification and HPLC as in preparation 2(*b*) to be deacetoxycephalosporin C], whereas the extracts from S.lividans 66: pIJ 702 and S.lividans 66: pBROC 148 were not able to carry out this transformation.

PREPARATION 3

The Location of the Isopenicillin N Synthetase Gene in the Cloned Flavobacterium DNA of pBROC 143

In order to confirm that the Flavobacterium sp. SC 12,154 DNA of pBROC 143 carried the isopenicillin N synthetase gene, plasmid DNA was probed with the Penicillium isopenicillin N synthetase gene using the technique of Southern hybridisation.

The Penicillium isopenicillin N synthetase gene DNA was obtained from David Smith and John H. Bull (Department of Microbiology, University of Bristol, Bristol, England) who isolated it by hybridisation from a gene bank of P. chrysogenum CMI 314652 using an oligonucleotide probe corresponding to nucleotides 205–264 of the Cephalosporium acremonium isopenicillin N synthetase gene as described by Samson et. al (Nature (1985) 318, 191–194, and European Patent Application Publication No. 0 200 425).
a) Probing a restriction enzyme digest of Flavobacterium sp. SC 12,154 total cellular DNA with the Penicillium isopenicillin N synthetase gene.

25 ng ($10^8$ dpm/µg) of $^{32}$p-labelled Bam HI/Xba I excised single stranded DNA fragment (approximately 0.9Kb in size, representing most of the isopenicillin N synthetase gene of P. chrysogenum CMI 314652) was used in a Southern hybridisation experiment with 1 µg of Bam HI digested total cellular DNA from Flavobacterium sp. SC 12,154.

Using Flavobacterium DNA bound to 'Gene Screen Plus' hybridization transfer membranes (as supplied by NEN Research Products), prehybridization and hybridization was carried out at 65° C. in 1% SDS. 1M sodium chloride, 10% dextran sulphate and denatured salmon sperm DNA (200 µg/ml) using all of the labelled probe.

After 16 hours incubation, unbound probe was washed from the membrane with 2.5 litres of 2×SSC, 0.1% SDS at 65° C. over a period of 3 hours. The membrane was then placed in contact with X-ray film for 14 days at −80° C. using an intensifying screen. Development of the film showed the presence on the hybridization membrane of a single intense band of radioactivity corresponding to a Bam HI fragment of Flavobacterium DNA of 6–7 Kb approximately in size, very similar to the size of the Bam HI Flavobacterium DNA fragment carried by pBROC 143.
b) Probing pBROC 143 DNA with the Penicillium isopenicillin N synthetase gene.

Samples of pBROC 143 DNA digested with several different combinations of restriction enzymes were probed with $^{32}$p-labelled Penicillium isopenicillin N synthetase gene DNA in a Southern hybridization experiment using identical conditions to those in Preparation 3*a*).

The probe bound strongly to only the smaller Bam HI/Sac I DNA fragment (approximately 1.3Kb in size as judged by agarose gel electrophoresis) of the Flavobacterium sp. SC 12,154 DNA carried in pBROC 143. It did not bind elsewhere in pBROC b 143.

This finding confirmed the presence of Flavobacterium sp. SC 12,154 DNA in pBROC 143 having a high degree of homology with the isopenicillin N synthetase gene of Penicillium chrysogenum CMI 314652.

PREPARATION 4

The Isolation of DNA Occurring Next to That DNA Contained in pBROC 143 from the Flavobacterium sp. SC 12,154 Chromosome a) Construction of a PMMB33 cosmid library of Flavobacterium sp. 12,154 total cellular DNA.

The Gram-negative cosmid pMMB33 was obtained from Dr F. C. H. Franklin, Genetics Department, University of Birmingham, Birmingham (UK). Its use to construct a library of Flavobacterium sp. SC 12,154 total cellular DNA was as described in detail for the construction of libraries of Pseudomonas total DNA by Frey et al (Gene [1983], 24 299–308).

We were able to obtain 10,000 colonies of *E.coli* DH1:pMMB33 clones, a sample of which were shown to contain approximately 35Kb Sau 3AI fragments of Flavobacterium DNA cloned onto the cosmid vector pMMB33.
b) Probing an *E.coli* DHI pMMB33 cosmid library of Flavobacterium total cellular DNA with the Flavobacterium DNA contained in pBROC 143.

25 ng of the 6.3Kb Bam HI fragment of pBROC 143 was radioactively labelled with phosphorus from $^{32}$p dCTP using the Multiprime kit commercially supplied by Amersham International, Amersham, UK. The *E.coli* DH1: pMMB33 cosmid library of Flavobacterium sp. SC 12,154 was replica plated onto 82 mm. Hybridization Transfer Membrane discs as supplied by NEN Research Products, 549 Albany Street, Boston, USA. The transferred colonies were lysed, prehybridized and hybridized at 65° C. with the radioactive probe as recommended by the manufacturers, NEN.

After overnight hybridization the membranes were washed with 2×SSC, 0.1% SDS at 65° C. for 3 hours and finally washed with 0.1×SSC at room temperature for 1 hour.

Exposure of the membranes to X-ray film for 24 hours revealed 37 colonies to which the pBROC 143 DNA had hybridized.

Figure 1:
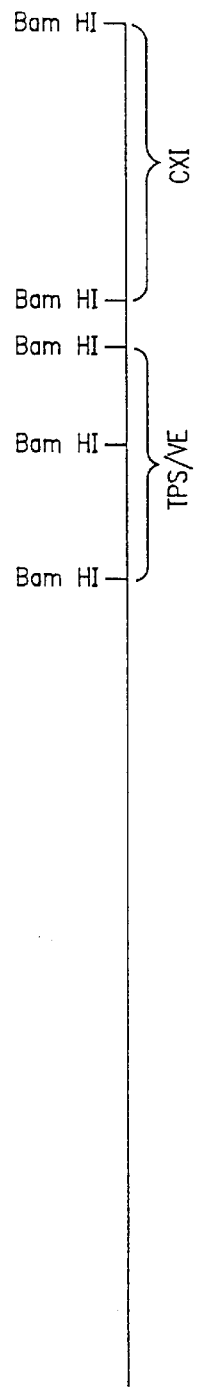
FIG. 1 is a restriction map of a portion of Flavobacterium sp. SC 12,154 DNA showing that region (marked TPS/VE) comprising one or more genes involved in the biolsynthesis of ACV and that region (marked CXI) which comprises cyclase, epimerase and expandase genes.

These colonies were isolated from the preserved library and their cosmid DNA content examined. It was found that only two of the hybridizing colonies would furnish preparations of undeleted cosmid DNA. When these cosmids (pBROC 155 and pBROC 156) were mapped with restriction endonucleases they were found to contain almost identical pieces of DNA but in opposite orientations on the cosmid pMMB33. The relevant portion of the DNA is shown in FIG. 1.

PREPARATION 5

Construction of a Library of S.clavuligerus ATCC 27064 DNA in pHC 79

10 μg of pHC 79 DNA (Hohn, B. and Collins, J (1980) Gene 11, 291–298) was digested to completion with restriction enzymes Sal I and Bam HI. A further 10 μg of pHC 79 DNA was digested to completion with Eco RI and Bam HI. To isolate the required 'cosmid arms' both digests were fractionated on a sucrose gradient (10–40%). The yield of each cosmid arm was >5 μg. 100 μg of S.clavuligerus ATCC 27064 chromosomal DNA was partially digested with Sau 3AI and fractionated on a sucrose gradient (10–40%). Fractions containing restriction fragments >30Kb and <50Kb were pooled thus providing approximately 10 μg of Sau 3AI fragments in this size range. These fragments were ligated to the cosmid arms at a molar ratio of 1:1:1 (DNA concentration 200 μg ml$^{-1}$). After 24 hours the ligation mix was packaged in vitro into lambda phage. (Phage lambda packaging extracts and protocol supplied by Amersham International PLC). Transfection of *E.coli* DHI (Low, B. (1968) PNAS 60, 161–167) yielded 5×10$^7$ transfectants/μg packaged DNA.

PREPARATION 6

Preparation of pBROC 381

5000 *E.coli* DHI colonies containing pHC 79 with S.clavuligerus ATCC 27064 DNA inserts were immobilized and lyzed on nitrocellulose filters. The 1.2 kb Bam HI –Kpn I ended fragment from pBROC 137[prepared as described in European Patent Application Publication No. 0 233 715; see also FIG. 5] was isolated and nick translated. This fragment was used to probe the filters by standard colony hybridisation techniques. Seven hybridising colonies were obtained, one of which (pBROC 371) contained the DNA segment illustrated in FIG. 5(*b*).

The 3.8 kb Bam HI–Bam HI fragment situated at the 'left hand end' of pBROC 371 DNA shown in FIG. 9 was subsequently sub-cloned, using standard methodology, into the Bam HI site of pAT 153. The resulting construct was designated pBROC 381.

PREPARATION 7

Probing the S.clavuligerus ATCC 27064 DNA Library

5000 *E.coli* DHI colonies containing p HC 79 with S.clayuligerus ATCC 27064 DNA inserts were immobilized and lyzed on nitrocellulose filters. The 3.8 kb Bam HI fragment from pBROC 381 was isolated and nick translated. The labelled fragment was used to probe the filters by standard colony hybridization techniques. Eleven hybridizing colonies were obtained four of which contained the DNA segment as illustrated in FIGS. 8–10. Mapping data of one of these cosmids pBROC 402, revealed that this DNA extended about 9 kb beyond the 'left hand end' of the DNA disclosed in FIG. 1 of European Patent Application Publication No. 0 233 715.

PREPARATION 8

Probing S.clavuligerus ATCC 27064 DNA with the Isopenicillin N Synthetase Gene from Penicillium Chrysogenum CMI 314652

(a) Chromosomal DNA

A 0.9 kb Xba I–Bam HI fragment of the isopenicillin N synthetase gene from Penicillium chrysogenum CMI 314652 (as describe din Preparation 3) was isolated and nick translated with $^{32}$p-dCTP. Bcl I and Bql II restriction endonuclease digests of S.clavuligerus ATCC 27064 were electrophoresed through agarose, transferred to a nitrocellulose filter, and probed with this 0.9 kp labelled fragment (Genetic Manipulation in Streptomyces: A laboratory manual, Hopwood et al 1985 published by the John Innes Foundation. The filter was twice washed in 2×SSC; 0.1% SDS for 30 minutes at 68° C. and exposed to X-ray film. After 96 hours exposure a single Bql I fragment (1.8 kb) and a single Bql II fragment (6.6 kb) were observed to hybridize to the probe.

(b) Cosmid cloned DNA

The cosmid pBROC 401 containing the DNA segment shown in FIG. 5(*c*) (see Preparation 7) was digested with Bcl I restriction endonuclease, electrophoresed through agarose and transferred to a nitrocellulose filter. The filter was probed with the labelled 0.9 kb fragment of the isopenicillin N synthetase gene as above. A 1.8 kb Bcl I fragment contained within the DNA of FIG. 10 was observed to hybridize to the probe. This fragment was of identical size to the Bcl I fragment of chromosomal DNA which hybridized to the probe.

PREPARATION 9

The Location of the Tripeptide (ACV) Synthetase Gene(s) Within Flavobacterium and S. clavuligerus DNA Penicillium chrysogenum produces the penicillins but not the cephalosporins. Thus the only antibiotic genes P.chrysogenum has in common with Flavobacterium sp. SC 12,154 are those genes concerned with the biosynthesis of isopenicillin N from its constituent amino acids. By probing Penicillium chrysogenum NRRL 1951 total chromosomal DNA with fragments of DNA from pBROC 155 (see FIG. 1) it was possible to determine two fragments [designated TPS/VE and CXI in FIG. 1] of Flavobacterium DNA in pBROC 155 which hybridized to P.chrysogenum NRRL 1951 DNA. As the approximate location of DNA coding for the isopenicillin N synthetase gene of Flavobacterium within pBROC 143 and so in pBROC 155 had already been identified (Preparation 3) it was possible to assign the other hybridizing fragment of pBROC 155 (fragment TPS/VE-see FIGS. 1 and 2) to the gene(s) involved in the biosynthesis of the ACV tripeptide.

Further evidence that the DNA fragment TPS/VE of pBROC 155 is involved in antibiotic biosynthesis and is the ACV synthetase gene(s) was provided by the hybridization of this DNA solely to a site on the S.clavuligerus total cellular DNA close to where the IPNS gene is located (see FIGS. 8–10 and Preparation 8).

a) Isolation of Penicillium chrysogenum NRRL 1951 total chromosomal DNA.

500 mls of a 40 hour shake flask culture of P.chrysogenum NRRL 1951 (grown in the conditions of Hamlyn P. F. et al, (*Enzyme Microb. Technol*, [1981] 3 321–325) was harvested by filtration through muslin on a Buchner funnel. It was washed well with water and then with a small volume of SSE buffer (Spermidine HCl 4 mM, Spermine HCl 1 mM. $Na_2EDTA$ 10 mM. Trisbase 10 mM. KCl 0.1 mM brought to pH 7.0 with HCl solution).

After squeezing the mycelium dry in the muslin it was mixed to a thin paste with 0.5×SSE, frozen rapidly in liquid nitrogen and ground in a pestle and mortar. On thawing at 65° C. the paste was filtered through Miracloth (supplied by Calbiochem and preboiled in 10 mM EDTA) washing through with 0.5×SSE to bring the total volume of homogenate to 40 Cml. The filtrate was centrifuged at 6000 g for 20 minutes at 4° C. to give a pellet of nuclei which was resuspended in 5 ml of 0.5×SSE, 0.2% Nonidet NP40 (Sigma) using a tissue grinder.

The suspension was incubated at room temperature with 0.55 ml 10% SDS, proteinase K 100 µg/ml, to lyse the nuclei and the mixture deproteinated with an equal volume of neutral phenol-chloroform. After the addition of ethanol at −20° C. the DNA was spooled out of solution onto a glass rod, dried briefly and resuspended in TE buffer.

b) Hybridization of fragments of pBROC 155 DNA to restriction endonuclease digests of Penicillium chrysogenum NRRL 1951 total chromosomal DNA.

25 µg of pBROC 155 plasmid DNA was digested to completion with Bam HI restriction endonuclease and all of the resulting fragments isolated after agarose gel electrophoresis. Each fragment (25 ng) was radioactively labelled with $^{32}p$ using the method described in Preparation 10) and used to probe samples of Bql II endonuclease restriction enzyme digested total chromosomal DNA of P. chrysogenum in Southern hybridization experiments using stringency conditions of 2×SSC, 0.1% SDS at 64°C.

Fragment CXI (see FIGS. 1–2) hybridized to a 5 kb Bql II fragment of Penicillium chrysogenum NRRL 1951 DNA. A similar Southern hybridization experiment using authentic Penicillium chrysogenum isopenicillin N synthetase DNA [as in preparation 8*a*)] as a probe showed hybridization to the same size of fragment. The two Bam HI fragments making up fragment TPS/VE (see FIGS. 1 and 2) hybridized to 8.5 kb and 5 kb Bql II generated fragments of Penicillium chrysogenum NRRL 1951 DNA. None of the other fragments of pBROC 155 DNA hybridized.

The cross hybridising region thought to correspond to the ACV synthetase was found to be on two contiguous Bam HI fragments of 3.0Kb and 2.2Kb in the Flavobacterium cosmid clone. These fragments were used as probes for the construction of cross hybridisation maps (see Preparation 10 and FIGS. 12–13).

c) Hybridization of fragment TPS/VE of pBROC 155 to S.clavuligerus 27064 DNA 25 ng of TPS/VE fragment DNA, labelled with 32 p as in Preparation 9*b*) was used as a probe in a Southern hybridization experiment against S.clavuligerus 27064 total cellular DNA digested with various restriction endonucleases using stringency conditions of 2×SSC, 0.1% SDS, 65°C.

It was observed that fragment TPS/VE hybridized only to one or two fragments of S.clavuligerus DNA.

When restriction endonuclease digestion fragments of pBROC 371 and pBROC 401 (see Preparations 6 and 7) were probed with $^{32}p$ labelled TPS/VE fragment DNA (using stringency conditions of 2×SSC, 0.1% SDS, 65°C.) only fragments at the 'left hand' end of pBROC 371 and at the 'right hand' end of pBROC 401 hybridized. Further Southern hybridizations in this manner delineated that portion of DNA [represented in FIG. 11] to which TPS/VE DNA hybridized.

PREPARATIONS 10–16

In Preparations 10–16 the materials and methods used were as follows:

Materials and Methods (a) Strains

P.chrysogenum

CMI 314652 is an oligomycin resistant, nicotinamide requiring strain, which has been deposited at the Commonwealth Mycological Institute under the terms of the Budapest Treaty. The deposit was made on Apr. 16, 1987.

CMI 317734 is a nicotinamide autotroph of wild type P. chrysogenum and was deposited at the Commonwealth Mycological Institute on Jul. 22, 1987.

*Escherichia coli*

DH1:recA; palA, hsr, hsm=, endoIB, relA1; DH5alpha: F−, endA1, hsdR17, (rk−,mk+), supE44, thi−1, −, recA1, gyrA96, φ 80 dlacZ m15. Strains were transformed according to the method of Hanahan *J. Mol. Biol*, 1983, 166, 557–580). NCIB 12591: Carries the cosmid pCX3.2 which contains the gene cluster shown in FIG. 13.

A. nidulans

NPA5: pyrG189, pyroA4, fwA1, npeA 0022.

(b) Isolation and Manipulation of DNA

Total DNA extraction from P.chrysogenum was as described by Ballance et al, *Biochem. Biophys, Res. Commun.*, 1983, 112, 284–289. Standard procedures were used for DNA manipulations including small scale plasmid isolation, restriction enzyme digestion, ligation, Southern analysis and *E.coli* colony hybridisation (Maniatis et al., (Molecular Cloning. A Laboratory Manual, Cold Spring Harbour Laboratory, Cold Spring Harbour, N.Y., 1982). DNA fragments were purified from agarose gels using a Geneclean kit (BIO 101 Inc., La Jolla, Calif., USA.) according to the manufacturer's instructions.

For gene library construction, total DNA from P.chrysogenum CMI 314652 was partially digested with the restriction enzyme Sau 3AI and size fractionated on a preparative agarose gel to give fragments of 35–40Kb. These fragments were ligated into the Bam HI site of the A.nidulans cloning vector pCAP2. Recombinant molecules were in vitro packaged into lambda particles and used to transfect *E.coli* DH1 to ampicillin resistance.

(c) A. nidulans Transformation

Transformation of A. nidulans was performed as described by Ballance and Turner (*Gene*, 1985, 36, 321–331).

(d) Penicillin Bioassays

Strains to be assayed were inoculated into 2 ml of FM medium (Holt and Macdonald, Antonio van Lesuwenhoek, 1968, 34, 409–416) contained in the well of a plastic tissue culture dish. After five days static incubation at 25° C., 100

μl of the broth was placed in the well of a nutrient agar plate seeded with the spores of Bacillus subtilis (1 ml of 2×10⁸ spores/ml per 100 ml) and 0.5 ml of 2% 2,3,5-triphenyltetrazolium chloride (TTC) per 100 ml. The plate was incubated at 30° C. overnight.

PREPARATION 10

Construction of a Cross Hybridisation Map Between Flavobacterium and P. chrysogenum with the Region of DNA Encoding the ACV Synthetase Gene The 3.0Kb Flavobacterium Bam HI fragment from Preparation 9(b) was used as a probe to screen 500 colonies of a P.chrysogenum CMI 314652 cosmid gene library prepared as described above. Five positively hybridising colonies were obtained. Restriction enzyme digestion of these clones indicated that four of them were identical and the fifth shared a considerable amount of sequence in common with these four. One of these clones, pCX3.2, was taken and analysed further. This clone contains approximately 38 kb of P. chrysogenum DNA in the cosmid vector pCAP2. Probing Southern blots of restriction enzyme digests of pCX3.2 with the P.Chrysogenum IPNS gene revealed that the IPNS gene was present on this cosmid. The blot was also probed with the Flavobacterium 3.0Kb Bam HI fragment which hybridised to a single 5.Kb Xho I band and a single Eco RI band of 8.0Kb; these fragments were subcloned into pUC19 to give pGXS11 and pGXE1 respectively.

A restriction map was constructed for both these subclones and for further subclones, and is shown in FIG. 13. pGX-C1overlaps with the P. chrysogenum IPNS gene cloned into the plasmid pUC9, the construct being designated as pCYX4.

The cosmid clone pCX3.2 carries not only the ACV and IPNS genes but additionally comprises the acyl transferase (ACT) of P. chrysogenum. The ACT gene is located within the sub-clone pGXB20 (See FIG. 13) as indicated by our own experiments showing an RNA transcript associated with this region, and as conformed by information about the location of the ACT gene of P. chrysogenum disclosed by A. E. Veenstra at the 4the American Society of Microbiology Meeting on the Genetics and Molecular Biology of Industrial Micro-organisms held in Bloomington, Id. from 2nd to 7the Oct., 1988.

Southern blots of restriction digests of the pCX3.2 subclones shown in FIG. 6(b) were probed with the 3.0Kb and 2.2Kb Flavobacterium DNA fragments from Preparation 9(b). The 3.0Kb fragment hybridised to the 3.5 kb Xho I–Sal I fragment marked GX1 in FIG. 13. The 2.2Kb fragment hybridised to the Xho I–Pst I fragment of the GX1 region as well as to two further areas marked GX2 and GX3. It would thus appear that if there are three distinct regions of homology between the Flavobacterium gene cluster and the P.chrysogenum cluster.

PREPARATION 11

Construction of a cross hybridisation map between P. chrysogenum and A. nidulans with the region of DNA encoding the ADV synthetase gene A cosmid library of total A. nidulans DNA constructed in the cosmid vector pCAP2 was probed with the Pst 1–Sal 1 fragment of pGXS11 (see FIGS. 12–13) containing the GX1 and GX3 DNA regions. Positively hybridising clones were identified. One cosmid clone so isolated was termed pNGX1 and mapped further using separate probes containing the GX1, GS2 and GX3 regions of P. chrysogenum cosmid clone pCX3.2. The resulting cross hybridisation map is shown in FIG. 14. The region of homology extends for approximately the same distance as that region in P. chrysogenum and GX1, GX2 and GX3 are in the same order relative to the transcription of the IPNS gene to which they are also linked.

Preparation 12

Demonstration that Sequences Homologous to the P. chrysogenum ACV Synthesis Gene(s) are Present in Cephalosporium acremonium Cephalosporium acremonium produces the cephalosporin class of beta-lactam antibiotics and therefore shares in common with P. chrysogenum, which produces the penicillins, the genes for the initial part of the biosynthetic pathway. These are the ACV synthetase and IPNS genes. Sequence analysis has shown that 74% homology exists at the nucleotide level between the C. acremonium and P. chrysogenum IPNS genes (Carr et al. Gene 48:257–266). A similar level of nomology may exist between the ACV synthetase genes; this would allow the ACV synthetase gene of P. chrysogenum isolated as described above to be used as a probe to isolate the equivalent gene from C. acremonium. In order to demonstrate this the following experiment was performed.

Plasmid pGXE1, a subclone on pCX3.2 (FIG. 13) containing the GX1, GX2 and GX3 (ACV synthetase) regions of P. chrysogenum, was labelled with 32 p and used as a probe against a Southern blot of a Bam HI digest of total DNA prepared from C. acremonium ATCC 11550. Stringency conditions were 2×SSC, 0.1% SDS at 55° C. Two hybridising bands were obtained at approximately 3.2 Kb and 5.1 Kb. A Southern blot of Bam HI digests of total DNA from the related filamentous fungi N. crassa NCP4 and A. niger AB4.1, which do not produce beta-lactams, was also probed with pGXE1; no hybridising bands were detected at the same stringency of hybridisation.

Preparation 13

Repair of a non-penicillin producing mutation in A. nidulans by pCX3.2

Evidence that DNA present in pCX3.2 (FIG. 13) is involved in synthesis of the ACV tripeptide was provided by the fact that the cluster could be used to repair a non penicillin producing mutation in A. nidulans.

pCX3.2 was used to transform directly an A. nidulans strain that possesses a mutation in a gene involved in its penicillin biosynthetic pathway. The strain in question NPA5, is blocked at the step of ACV synthesis (npeA0022) (Makins et at., J. Gen. Microbiol., 1981, 122, 339–343.)

Transformants of NPA5 when assayed for their penicillin producing ability were negative when transformed with pPCY7 (a plasmid capable of transforming A. nidulans and carrying the P. chrysogenum IPNS gene) but three out of the five pCX3.2 transformants tested were positive for penicillin production. They produced zones of inhibition on a bioassay plate varying from slightly less than wild type to slightly greater than the non-producing controls. The zones were penicillinase sensitive. The reasons for the variability of the zone size in the transformants obtained with pCX3.2 are not clear but may be due to the fact that A. nidulans transformants containing P. chrysogenum DNA are affected by the presence of the foreign DNA as they show a reduced growth rate. In this state they may be unable to produce wild type levels of penicillin.

these results indicate that the gene cluster isolated from *P. chrysogenum* can restore the ability of a strain of *A. indulans* which is blocked in the synthesis of ACV to produce penicillin.

Preparation 14

Demonstration of Elevated Levels of ACV-Synthetase Enzyme Activity in Transformers of *P. chrysogenum* CMI 317734 Co-Transformed with pCX3.2 and p3SR2.

Enzymic preparations of *P. chrysogenum* CMI 317734 and from transformants thereof co-transformed with either pCX3.2 or p3SR2 were used to determine the levels of ACV-Synthetase activity.

*P. chrysogenum* CMI 317734 and transformants thereof were used to inoculate 250 ml shake-flasks at $10^5$ spores per ml containing 20 ml seed medium consisting of 35 g per liter corn steep liquor, 15 g per liter glucose, 5 g per liter $CaCO_3$ and 8 g per liter rape seed oil pH 5.9. Shake-flasks were grown for 2 days at 25° C., 260 rpm, and used to inoculate final-stage shake-flasks containing 20 ml 85 g per liter lactose, 35 g per liter corn steep liquor, 6 g per liter phenoxyacetic acid, 10 g per liter $CaCO_3$, 6 g per liter rape seed oil pH 6.0 (10% cross).

The final-stage shake-flasks were then grown for one or two days under similar conditions before harvest.

To harvest, the contents of 2 to 3 shake-flasks were pooled, filtered on a 5.5 cm GF/A disc and washed with 200 ml ice-cold isotonic saline. The mycelial pad was then immersed in 12 ml extraction buffer (0.1 M-MOPS, pH 7.5, 50 mM-KCl, 20 mM-EDTA, 30 mM-2 mercaptoethanol, 50% glycerol (V/V) and sonicated for 4 bursts of 20 seconds with a half-inch horn on an Ultrasonics W-385 sonicator at power setting 6. The sonicated extract was centrifuged at 40,000 g for 20 minutes and 2 ml supernatant desalted on a PD-10 Sephadex™ column pre-equilibrated with buffer similar to extraction buffer except that the glycerol content was 20% (V/V). The fractions containing protein were pooled and used for the assay.

The assay for ACV-synthetase was based on the methods of Jensen et al (FEMS Microbiol Letts. [1988 ] 49, 213–218) and Banko and Demain (J. Am. Chem. Soc. [1988] 109, 2858–2860).

The incubation mixture was as described by Banko and Demain except that the protease inhibitor, Aprotinin, was included at 1 mg per ml. Incubation times varied between 120 and 240 minutes. As controls, incubation mixtures were also stopped at time zero and chromatographed.

The methods of derivatisation using Thiolyte MB™ and of separation by HPLC and detection by fluorimetry was as described by Jensen et al but for the following changes. The pH of the sodium acetate elution buffer was reduced to 4.4. The first five minutes of elution were isocratic at 90:10 (V/V) sodium acetate:methanol. Between 5 minutes and 35 minutes a linear gradient from 90:10 to 55:45 sodium acetate:methanol was employed.

Elution of ACV (in its reduced monomeric form due to the inclusion of 0.5 mM—dithiothreitol in the standard) was observed with a retention time of 29.5 minutes. A sensitivity of 0.1 nmols ACV was achieved.

Significantly elevated levels of ACV-synthetase were consistently detected in a transformants of CMI 317734 transformed with pCX3.2 compared to CMI 317734 transformed with p3SR2 which lacks the *Penicillium chrysogenum* DNA sequence present in pCX3.2.

In this manner it was possible to shown that the approximately 38 Kb insert of *P. chrysogenum* DNA contained in pCX3.2 contains a gene or genes that directly affect the level of ACV-synthetase enzymic activity.

Preparation 15

Demonstration of Elevated Levels of ACV-Synthetase Enzymic Activity in Transformants of *P. chrysogenum* CMI 317734 Transformed with pPEN3.

The plasmid vector pPEN3 was constructed which like pCX3.2 contains sequences GX1, GX2 and GX3 (regions homologous with ACV-synthetase genes of Flavobacterium sp). but lacks the IPNS gene and the ACT gene. This was done by subcloning the Eco Rl fragment from pGXE1 onto p3SR2. This vector was then used to transform CMI 317734 and transformants were assayed for ACV-Synthetase activity. Extraction and enzyme assays were as described in Preparation 14.

Elevated levels of ACV-synthetase were measured in transformants when compared to CMI 317734 and a transformants of CMI 317734 transformed with p3SR2 alone.

In this manner it was possible to demonstrate that the 8.0 Kb insert of *P. chrysogenum* DNA contained in pPEN3 contains a gene or genes that directly affect the levels of ACV-synthetase.

Preparation 16

Heterologous expression of the *P. chrysogenum* ACV Synthetase Gene in *Neurospora crassa* and *Asperqullus niger*

*N. crassa* and *A. niger* produce no detectable beta-lactams and have no DNA sequences closely homologous to the ACV synthetase, isopenicillin N synthetase (IPNS) or acyltransferase (ACT) genes of *P. chrysogenum*. Given the known high homology of these genes with other beta-lactam producers (Weigel et al. *J. Bacteriology*, 1988, 170, 3817–3826) it can be assumed that these fungi do not possess genes encoding penicillin biosynthetic enzymes.

Expression of the *P. chrysogenum* ACV synthetase gene in *N. crassa* and *A. niger* was used to demonstrate the presence of this and all other genes essential for penicillin biosynthesis in the cosmid clone pCX3.2 [see Preparation 10 and FIG. 13].

a) Transformation of *N. crassa* with pCX3.2.

pCX3.2 which contains the pyr-4 gene of *N. crassa*, was used to transform *N. crassa* NCP4, a pyr-4 auxotroph, to prototrophy by the method of Vollmer and Yanofsky (*Proc. Nat. Acad. Sci.*, 1986, 83, 4869–4873). Transformants were purified 3 times by streaking on selective medium and spores used to inoculate 50 ml of FM modified medium. After 3 days growth at 30° C., with shaking, 150 µl of the fermentation broth was bioassayed suing standard techniques. Four out of the 20 transformants tested produced zones of antibiosis against *Bacillus subtilis*; these zones were penicillinase sensitive. The parent strain, NCF4, gave no zone.

Two of the transformants PCX1 and PCX5 and the parent NCP4 were further tested for production of antibiotic by bioassay against *Bacillus calidolactis* C953 (at a concentration of $0.5 \times 10^7$ spores per ml in tryptone soya agar, incubated at 46° C. overnight. Standards of 10 mg to 1 μg per ml were included with a linear relationship always observed.

Results indicated that PCX1 produced penicillin to a concentration of 170 ng per ml and PCX5 to 64 ng per ml. No penicillin was detected under similar conditions in NCP4.

The penicillin V produced was authenticated by HPLC after derivatisation with 1-hydroxybenzotriazole as described by Shah et al. [1988] Analyst 113 1197–1200.

The three enzymes ACV-Synthetase, IPN-Synthetase and Acyltransferase were assayed in these three cultures. All three were inoculated directly into final-stage medium (see Preparation 14) at a concentration of $10^6$ spores per ml and incubated at 30° C. at 260 rpm for 24 to 48 hours.

For ACV-Synthetase and Acyltransferase the method of extraction was similar to that described in Preparation 14. For IPN-Synthetase the method of extraction was similar but that the extraction buffer consisted of 30 mM-Tris HCl pH 8.0, 0.1 mM-DTT and 1.0 mM phenylmethylsulfonyl flouride and the PD-10 column was pre-equilibrated with this buffer.

The incubation conditions for ACV-Synthetase were as described in Preparation 14. The incubation conditions for Acyltransferase were as described by Luengo et al [1986] J Antibiotics XXX, IX, 1565–1573. Incubations were for 120 mins. The penicillin produced was measured by bioassay against Bacillus calidolactis as described above except that penicillin G was used as standard. The incubation conditions for IPN-Synthetase were as described by Ramos et al [1985] Anti. Microb. Agents. Chemother. 27 380–387. The incubations were for 120 mins. The IPN produced was measured by bioassay against Bacillus calidolactis as described above except that IPN at concentration of between 0.1 and 10 μg per ml were used as standards.

Measurements made are given in Table 1. All three enzymes were detected in both PCX1 and PCX5 but were absent or present at a very low level in the control.

TABLE 1

Enzyme Activities In Transformants of *Neurospora crasse* NCP4 Transformed with pCX3.2.

| Strain | ACV-Synthetase | IPN-Synthetase* | Acyltransferase* |
|---|---|---|---|
| PCX 1 | + | 20 | 389 |
| PCX 5 | + | 39 | 364 |
| NCP4 (control) | − | 0 | 0.5 |

*nmol per minute per g protein

Southern blot analysis of PCX1, PCX5 and NCP4 showed that PCX1 and PCX5 contained intact pCX3.2 DNA including those regions containing the ACV synthetase, IPNS and ACT genes. NCP4 had no homology with the P. chrysoqenum DNA contained in pCX3.2.

The above results demonstrate that pCX3.2 contains all the genes required for the biosynthesis of penicillin from primary amino acids and must therefore contain the ACV synthetase gene as well as the known IPNS and ACT genes. pCX3.2 may also contain other necessary unidentified genes and regulatory genes.

b) Transformation a A. niger with pCX3.2

A. niger AB4.1, a pyrG auxotroph, was transformed with pCX3.2 using the method of Yelton et al. Proc. Nat. Acad. Sci., 1984, 81, 1470–1474. The resulting transformants were purified and bioassayed for penicillin production as described above. Of the 4 transformants tested 3 produced zones of antibiosis against B. subtilis which were considerably reduced after treatment with penicillinase; the parent strain gave only a small penicillinase resistant zone.

Three of the transformants AN33, AN34 and AN36 and the parent AB4.1 were further tested for production of antibiotic by bioassay against Bacillus calidolactis C953 as described in Preparation 16(a). Results indicated that AN33, AN34 and AN36 produced penicillin to a concentration of 1.3, 0.8 and 2.3 μg per ml respectively. No penicillin was detected under similar conditions in AB4.1.

The penicillin V produced was authenticated by HPLC after derivatisation with 1-hydroxybenzotriazole as described by shah et al [1988] 113 1197–1200.

The three enzymes ACV-Synthetase, IPNS and ACT were assayed in these four cultures by methods similar to those described in Preparation 16(a).

Measurements are given in Table 2. Activities of ACV-Synthetase are given only as positive or negative due to the difficulty in quantifying the ACV detected. All three transformants possessed enzyme activity while AB4.1 did not IPN-Synthetase activity was also found in the three transformants but was not found in AB4.1 Acyltransferase activity was detected at a low level in AB4.1 but was very significantly higher in all three transformants.

TABLE 2

Enzyme Activities In Transformants of *Aspergillus niger* AB4.1 Transformed with pCX3.2.

| Strain | ACV-Synthetase | IPN-Synthetase* | Acyltransferase* |
|---|---|---|---|
| AN33 | + | † | 28 |
| AN34 | + | 3.0 | 16 |
| AN36 | + | 14.5 | 18 |
| AB4.1 (control) | − | 0 | 0 |

*nmol per minute per g protein
†not assayed

Southern blot analysis of total DNA from 2 of the transformants. ANN33 and AN34, showed that they contained intact pCX3.2 DNA whereas the parent strain had no homology with the P. chrysogenum DNA contained in pCX3.2 AN36 was not tested.

The above results demonstrate that pCX3.2 contains all the genes required for the biosynthesis of penicillin from primary amino acids and must therefore contain the ACV synthetase gene as well as the known IPNS and ACT genes. pCX3.2 may also contain other necessary unidentified genes and regulatory genes.

What is claimed is:

1. An isolated DNA construct that increases or improves the levels of a synthetase that generates δ(L-aminoadipyl)-L-cysteinyl-D-valine (ACV) when used to transform a suitable host cell, said isolated DNA construct comprising a DNA sequence selected from:

(a) a DNA construct contained in pCX3.2 having the configuration of restriction sites shown in FIG. 13 and encoding a polypeptide with ACV synthetase activity;

(b) a restriction fragment of the DNA construct of (a) comprising an intact gene encoding a polypeptide with ACV synthetase activity; and (c) a DNA construct endogenous to Penicillium, Flavobacterium or Streptomycin hybridisable to the DNA construct of (a) or the restriction fragment of (b) and encoding a polypeptide with ACV synthetase activity.

2. The DNA construct of claim 1 that contains a gene encoding acyl transferase.

3. The DNA construct of claim 1 that contains the entire biosynthetic gene cluster for the production of penicillin in a fungal host.

4. A recombinant vector comprising the DNA construct of claim 2.

5. The isolated DNA of claim 1, wherein said DNA is endogenous to *P. chrysogenum*.

6. The recombinant vector of claim 4, comprising the entire biosynthetic gene cluster for the production of penicillin in a fungal host.

7. A host transformed with the vector of claim 4.

8. A method of producing a penicillin in a fungal host cell which is naturally a non-producer of penicillins, which method comprises the steps of:

A. providing the recombinant vector as defined by claim 4;

B. transforming said fungal host with said recombinant vector; and

C. cultivating said transformed host under conditions effective to produce said penicillin.

9. A method of (i) increasing production of δ(L-aminoadipyl)-L-cysteinyl-D-valine from a fungal host cell which is naturally a producer of penicillin or (ii) unblocking or creating production of δ(L-aminoadipyl)-L-cysteinyl-D-valine from a non-producing mutant of said host blocked at the step of synthesizing δ(L-aminoadipyl)-L-cysteinyl-D-valine, which method comprises the steps of:

(a) transforming said fungal host or non-producing mutant thereof with a vector as defined by claim 4 and (b) cultivating the transformants so formed under conditions effective to produce or increase production of said δ(L-aminoadipyl)-L-cysteinyl-D-valine.

10. The recombinant vector of claim 4, wherein the vector is pCX3.2.

11. The transformed host of claim 1, wherein the DNA of the transformed host contains the entire biosynthetic gene cluster of the production of penicillin in a fungal host.

12. The host of claim 7 which is a fungal host.

13. The host of claim 7, wherein the host is *P. chrysogenum*.

14. The method of claim 8, wherein the recombinant vector is pCX3.2, deposited in an *E. coli* strain under accession number NCIB 12591.

15. The method of claim 8, wherein said penicillin produced is penicillin G or penicillin V.

16. The method of claim 9, wherein the host is *P. chrysogenum*.

17. The strain NCIB 12591.

* * * * *